(12) United States Patent
Ren et al.

(10) Patent No.: US 11,414,414 B2
(45) Date of Patent: Aug. 16, 2022

(54) PYRROLOQUINOLINE QUINONE GLYCINE BETAINE SALT

(71) Applicant: SHANGHAI XUANCHUANG BIOLOGICAL TECHNOLOGY CO., LTD., Shanghai (CN)

(72) Inventors: Guobin Ren, Shanghai (CN); Jinyao Chen, Shanghai (CN)

(73) Assignee: SHANGHAI XUANCHUANG BIOLOGICAL TECHNOLOGY CO., LTD., Shanghai (CN)

( * ) Notice: Subject to any disclaimer, the term of this patent is extended or adjusted under 35 U.S.C. 154(b) by 317 days.

(21) Appl. No.: 16/472,875

(22) PCT Filed: Feb. 6, 2018

(86) PCT No.: PCT/CN2018/075493
§ 371 (c)(1),
(2) Date: Nov. 12, 2019

(87) PCT Pub. No.: WO2018/113800
PCT Pub. Date: Jun. 28, 2018

(65) Prior Publication Data
US 2020/0385380 A1 Dec. 10, 2020

(30) Foreign Application Priority Data
Dec. 22, 2016 (CN) .......... 201611200767.4

(51) Int. Cl.
*C07D 471/04* (2006.01)
*C07C 229/12* (2006.01)

(52) U.S. Cl.
CPC .......... *C07D 471/04* (2013.01); *C07C 229/12* (2013.01); *C07B 2200/13* (2013.01)

(58) Field of Classification Search
CPC ..................................................... C07D 471/04
See application file for complete search history.

(56) References Cited

U.S. PATENT DOCUMENTS

2010/0035904 A1* 2/2010 Sun ...................... C07D 239/64
514/270
2013/0253001 A1* 9/2013 Ikemoto ............... C07D 471/04
514/292

* cited by examiner

*Primary Examiner* — Theodore R. Howell
*Assistant Examiner* — George W Kosturko
(74) *Attorney, Agent, or Firm* — Houtteman Law LLC

(57) ABSTRACT

Provided are a pyrroloquinoline quinone glycine betaine salt and a crystalline form thereof. The pyrroloquinoline quinone glycine betaine salt has the advantages of high solubility, good stability, a simple preparation process and low solvent residue.

7 Claims, 6 Drawing Sheets

PYRROLOQUINOLINE QUINONE GLYCINE BETAINE SALT

CROSS-REFERENCE TO RELATED APPLICATIONS

This application claims to the priority and the benefit of Chinese Invention Patent Application No. 201611200767.4, filed on Dec. 22, 2016, the entirety of which is incorporated herein by reference.

TECHNICAL FIELD

The present invention relates to a pyrroloquinoline quinone betaine salt and a crystalline form thereof, a method for preparation and application thereof.

BACKGROUND OF THE INVENTION

Pyrroloquinoline quinone (abbreviated as PQQ, as shown in formula (III)) is a possible new vitamin (Nature, vol. 422, Apr. 24, 2003, p. 832), and has attracted much attention as a useful material for dietary supplements, cosmetics, etc.

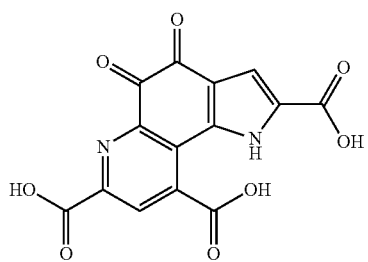

(III)

PQQ not only exists in bacteria, but also exists in eukaryotic molds and yeasts, and plays an important role as coenzyme. In addition, PQQ has been found to have many physiological activities. For example, PQQ can stimulate rapid growth of cells of microorganisms, plants, animals and humans; PQQ can remove redundant free radicals in a body and protect the body from oxidative damages; PQQ can play a role in term of neurotrophy and neuroprotection, such as in the treatment of Parkinson's disease, senile dementia and the like; PQQ can accelerate the oxidation of acetaldehyde to acetic acid to reduce the content of acetaldehyde in the body, so it is expected to reduce the toxicity damage to liver caused by alcohol drinking; oral administration of PQQ can effectively reduce the levels of lead in blood, brains and livers, and does not cause loss of beneficial metal elements including zinc and copper in the body; PQQ also promotes rapid wound healing in the case of skin burns caused by radioactive materials.

Betaine (trimethylglycine) is a natural alkaloid, which widely exists in animals, plants and microorganisms, and plays a physiological role as an osmotic pressure regulator and a methyl donor. Its regulation of osmotic pressure can protect cells, proteins and enzymes from environmental stress; and as a methyl donor, it can regulate a liver fat metabolism and protect livers. Betaine also contributes to antioxidation and neuroprotection, meanwhile, serves as an important component of drugs and dietary supplements for improving and treating cardiovascular diseases. In the food industry, betaine is widely used in production of food and fruit juice because of its moderate taste and colorless appearance. Due to its good stability, water solubility and moisture retention, betaine is also used in cosmetics and the like.

Pyrroloquinoline quinone in solid state as currently reported includes: PQQ in the free form (CN 102596952 A), sodium salt of PQQ (CN 102471336 A), lithium salt of PQQ (CN 101851234 A), calcium salt of PQQ (CN 103119044 A), choline salt of PQQ (CN 103261197 A) and the like. By comparing the physical properties of different salts, it has been found that the solubility of choline salt increased with the increase of the ratio of choline, however, resulting in an excess of choline intake, and a poor stability and hygroscopicity. The solubility of other metal salt forms are generally low, and the problem of metal ion intake also exists. In addition, during the preparation of salt forms of PQQ, a large amount of organic solvent is usually needed, resulting in a difficulty to remove solvent residue, furthermore, the long preparation time and high cost are disadvantages to industrial production.

SUMMARY OF THE INVENTION

The present invention provides a novel salt of pyrroloquinoline quinone, i.e. pyrroloquinoline quinone betaine salt and crystalline forms thereof, a method for preparation and application thereof.

A first aspect of the present invention provides a pyrroloquinoline quinone betaine salt of formula (I)

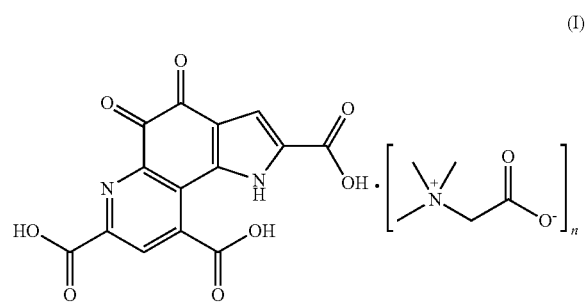

(I)

Wherein n is 0.5 to 3.

A second aspect of the present invention provides a crystalline Form A of pyrroloquinoline quinone betaine salt of formula (II)

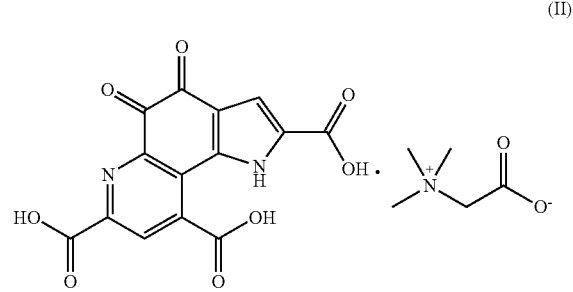

(II)

which has an XRPD pattern having diffraction peaks at $2^\theta$ of 6.721, 13.424, 16.941, 19.28, 21.7, 22.42, 27.5, 28.36, with the error range of the $2^\theta$ values being ±0.2.

The Form A of pyrroloquinoline quinone betaine salt of the present invention has an XRPD pattern substantially the same as FIG. 1 of the accompanying drawings.

A third aspect of the present invention provides a method for preparation of the pyrroloquinoline quinone betaine salt of formula (I), comprising the following steps:

(1) dissolving pyrroloquinoline quinone in an organic solvent, and adding betaine thereto to obtain a suspension;

(2) stirring the suspension at 25-35° C., then filtering and drying to obtain a solid.

In a preferred method of preparing the pyrroloquinoline quinone betaine salt, the organic solvent is ethanol.

A fourth aspect of the present invention provides a composition comprising the pyrroloquinoline quinone betaine salt of formula (I), and one or more pharmaceutically acceptable carriers, excipients or diluents, wherein n is 0.5 to 3.

The pyrroloquinoline quinone betaine salt and the Form A thereof provided by the present invention have a high solubility in water, a good stability and a low hygroscopicity, and therefore are superior to the existing salts of PQQ; the preparation process for the same is simple, and solvent residue thereof is low; both PQQ and betaine nutrients can be offered simultaneously, the intake of other substances can be reduced, so it is advantageous for use in the pharmaceutical compositions.

DETAILED DESCRIPTION OF THE INVENTION

The present invention provides a pyrroloquinoline quinone betaine salt.

As used herein, "pyrroloquinoline quinone" and "PQQ" have the same meaning and refer to pyrroloquinoline quinone of formula (III). With regard to the preparation method of PQQ, reference can be made to the method disclosed in JP 2751183B2. A first aspect of the present invention provides a pyrroloquinoline quinone betaine salt of formula (I), wherein n is 0.5 to 3, that is, the molar ratio of PQQ to betaine is 1:0.5 to 1:3. n is preferably from 0.6 to 2, more preferably from 0.8 to 2, most preferably 1. In other embodiments, the molar ratio of PQQ to betaine may also be any ratio within the above ranges, such as 3:2, 4:3, 2:3, 2:5, 3:4, 3:5, 3:7, 4:5, 4:7, 4:9, etc.

In the betaine salt of PQQ prepared by the prevent invention, the value of n can be determined by the raw material ratio of the added PQQ to betaine. When n=1, the obtained betaine salt of PQQ has a good stability and water solubility.

A second aspect of the present invention provides a crystalline Form A of pyrroloquinoline quinone betaine salt of formula (II), characterized in that it has an XRPD pattern having diffraction peaks at 2θ of 6.721, 13.424, 16.941, 19.28, 21.7, 22.42, 27.5, 28.36, with the error range of the 2θ values being ±0.2.

The pyrroloquinoline quinone betaine salt of formula (II) is a specific form of formula (I) when n=1.

Figure 1:
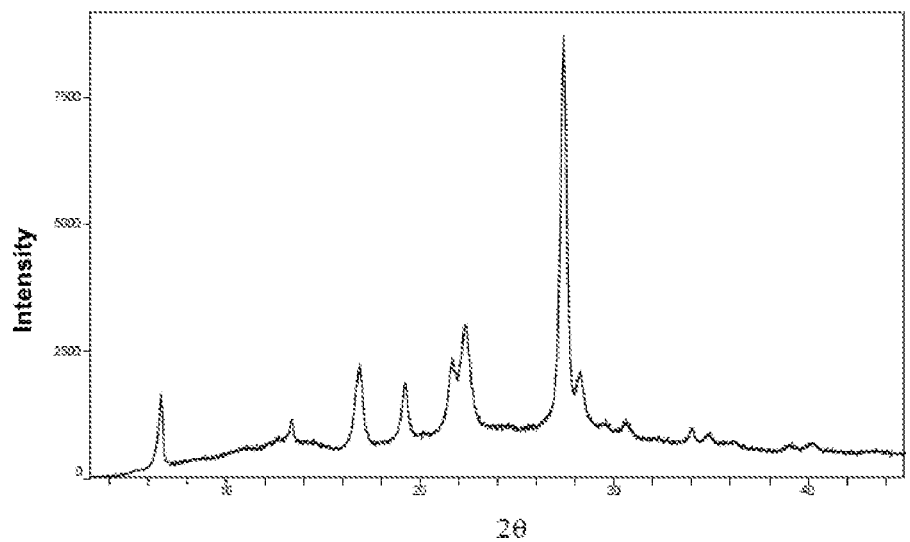
FIG. 1 shows an XRPD pattern of the crystalline Form A of pyrroloquinoline quinone betaine salt provided by the present invention.

The crystalline Form A of pyrroloquinoline quinone betaine salt of the present invention has an XRPD pattern substantially the same as FIG. 1 of the accompanying drawings.

A third aspect of the present invention provides a preparation method of the pyrroloquinoline quinone betaine salt of formula (I), characterized by comprising the steps of:

(1) dissolving pyrroloquinoline quinone in an organic solvent, then adding betaine thereto to obtain a suspension;

(2) stirring the suspension at 25-35° C., then filtering and drying to obtain a solid.

Wherein, the organic solvent is capable of dissolving PQQ in the free form. Organic solvents that can be used include common solvents such as methanol, ethanol, acetone, acetonitrile, dichloromethane, dimethylformamide, dimethylsulfoxide, and the like. In addition, the betaine salt of PQQ is slightly soluble in the organic solvent. In particular embodiments, the most preferred organic solvent is ethanol.

More specifically, the preparation method of the form A of the betaine salt of pyrroloquinoline quinone of formula (II) comprises the following steps:

(1) dissolving pyrroloquinoline quinone in ethanol, and adding about equal molar betaine thereto to obtain a suspension;

(2) stirring the suspension at 25-35° C. for 24 hours, then filtering and drying under vacuum at room temperature to obtain a red powder, i.e. the crystalline Form A of pyrroloquinoline quinone betaine salt of formula (II).

A fourth aspect of the present invention provides a composition comprising the pyrroloquinoline quinone betaine salt of formula (I), and one or more pharmaceutically acceptable carriers, excipients or diluents, wherein n is 0.5 to 3.

The betaine salt of PQQ in the composition of the present invention may be prepared according to the preparation method provided in the third aspect of the present invention.

Hereinafter, the present invention will be described in detail according to embodiments and with reference to the accompanying drawings. The foregoing and other aspects of the present invention will be apparent from the following detailed description. The scope of the prevent invention is not limited to the following examples.

Example 1-5

Preparation of Pyrroloquinoline Quinone Betaine Salt 50 mg of the raw material PQQ in the free form was weighed into a vessel, to the vessel, 5 mL of ethanol was added, and then the amount of betaine according to Table 1 (each in analytically pure) was added respectively to form a suspension. By maintaining temperature at 25-35° C., stirring for 24 hours, filtering and drying under vacuum at room temperature, a red powder was given. The yield was calculated by weighing and the results are shown in Table 1.

TABLE 1

Preparation of Pyrroloquinoline Quinone Betaine Salt

| EXAMPLES | Betaine (mg) | n in formula (I) | Yield |
|---|---|---|---|
| 1 | 18 | 1 | 81% |
| 2 | 9 | 0.5 | 79% |
| 3 | 15 | 0.8 | 78% |
| 4 | 39 | 2 | 79% |
| 5 | 54 | 3 | 80% |

Example 6

Characterization of Crystalline Form A of Pyrroloquinoline Quinone Betaine Salt by XRPD The X-ray powder diffraction (XRPD) pattern was measured using a Rigaku Ultima IV multipurpose X-ray diffractometer with the specific information collected as follows: Cu anode (40 kV, 40 mA), a scanning speed of 20°/min, a scanning range of (a range of 2θ) 3-45°, a scanning step size of 0.02, a slit width of 0.01. Samples were treated by pressing directly on the test plate using glass slides.

The XRPD pattern of the crystalline Form A of betaine salt of pyrroloquinoline quinone prepared according to the method described in Example 1 was determined to have diffraction peaks at 2θ of 6.721, 13.424, 16.941, 19.28, 21.7, 22.42, 27.5, 28.36, as shown in FIG. 1. The error range of 2θ values was ±0.2, and can also be ±0.15 by detection.

Those skilled in the art will appreciate that these diffraction peaks do not represent an exhaustive list of the diffraction peaks shown for the crystalline Form A of pyrroloquinoline quinone betaine salt. The 2θ value of the X-ray powder diffraction pattern can vary slightly with machine and with variations in the sample preparation and batch-to-batch variations, and the cited values are not considered as absolute values. It should also be understood that the relative intensities of the peaks may vary with orientation effects, and therefore the intensities shown in the XRPD traces encompassed by the present invention are exemplary and not intended for absolute comparisons.

Example 7

Figure 2:
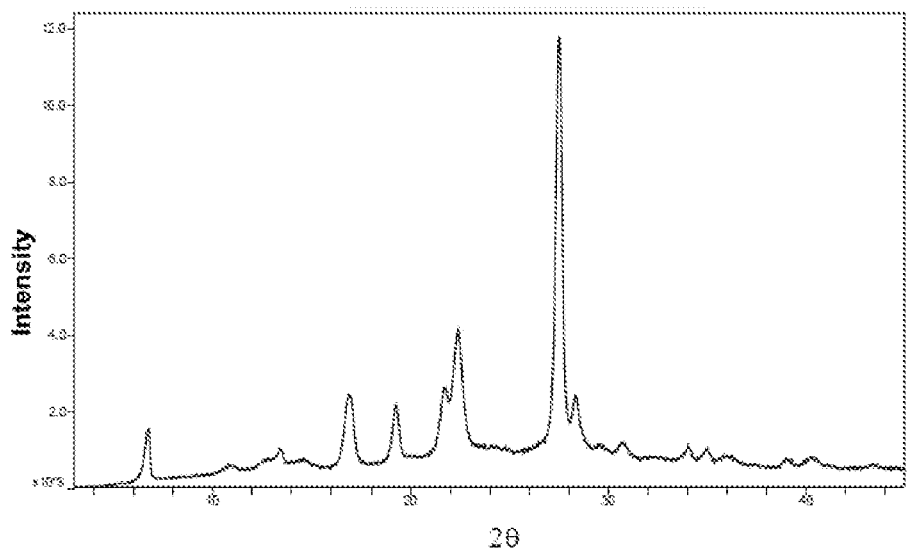
FIG. 2 shows an XRPD pattern of the high temperature stability of 5 days for the crystalline Form A of pyrroloquinoline quinone betaine salt provided by the present invention.
Figure 3:
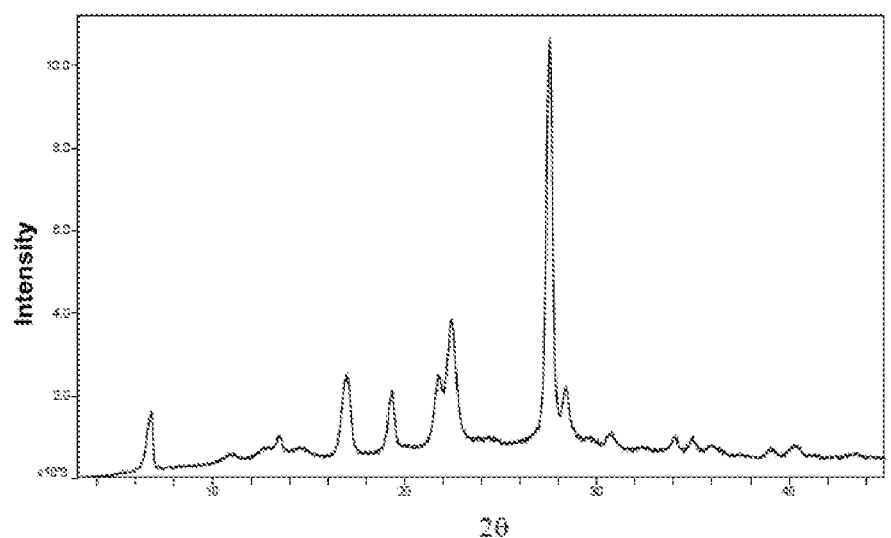
FIG. 3 shows an XRPD pattern of the high temperature stability of 10 days for the crystalline Form A of pyrroloquinoline quinone betaine salt provided by the present invention.

Study on High Temperature Stability of Crystalline Form A of Pyrroloquinoline Quinone Betaine Salt An appropriate amount of sample of the crystalline Form A of Pyrroloquinoline Quinone Betaine Salt was placed in an oven at 60° C., and after 5 days and 10 days the sample was removed for XPRD testing (as shown in FIGS. 2 and 3) to examine the crystalline stability of the sample against temperature. The results showed that the crystalline Form A of pyrroloquinoline quinone betaine salt was stable at high temperature.

Example 8

Figure 4:
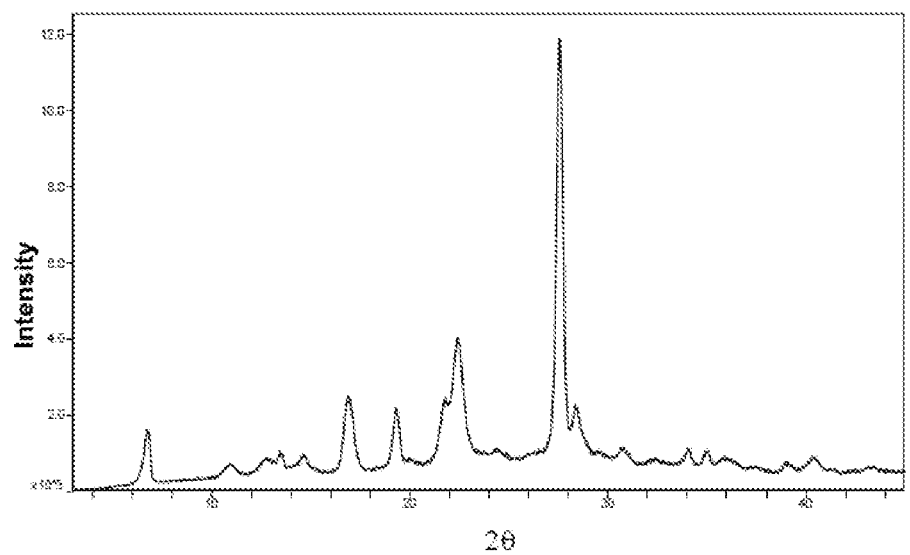
FIG. 4 shows an XRPD pattern of the high humidity stability of 5 days for the crystalline Form A of pyrroloquinoline quinone betaine salt provided by the present invention.
Figure 5:
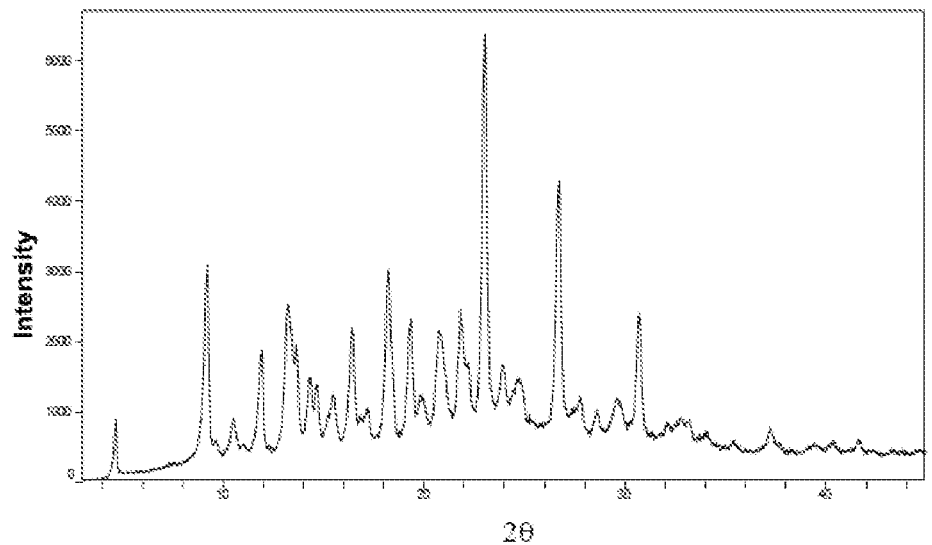
FIG. 5 shows an XRPD pattern of the high humidity stability of 10 days for the crystalline Form A of pyrroloquinoline quinone betaine salt provided by the present invention.

Study on High Humidity Stability of Crystalline Form A of Pyrroloquinoline Quinone Betaine Salt The appropriate amount of sample of the crystalline Form A of pyrroloquinoline quinone betaine salt is subjected to the humidity of 92.5%, and after 5 days and 10 days the samples were removed for XPRD testing (as shown in FIGS. 4 and 5) to examine the crystalline stability of the sample against humidity. The results showed that the crystalline Form A of pyrroloquinoline quinone betaine salt was stable under high humidity.

Example 9

Figure 6:
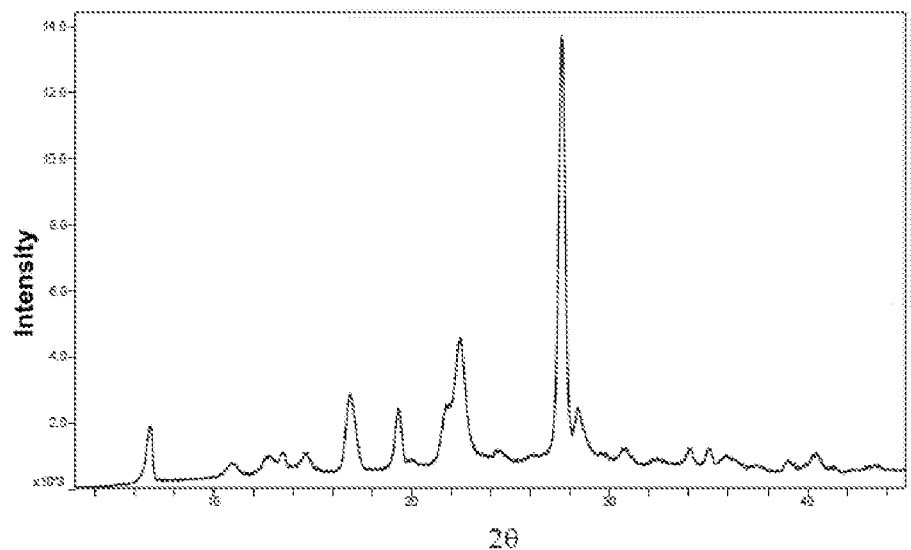
FIG. 6 shows an XRPD pattern of the illumination stability of 5 days for the crystalline Form A of pyrroloquinoline quinone betaine salt provided by the present invention.
Figure 7:
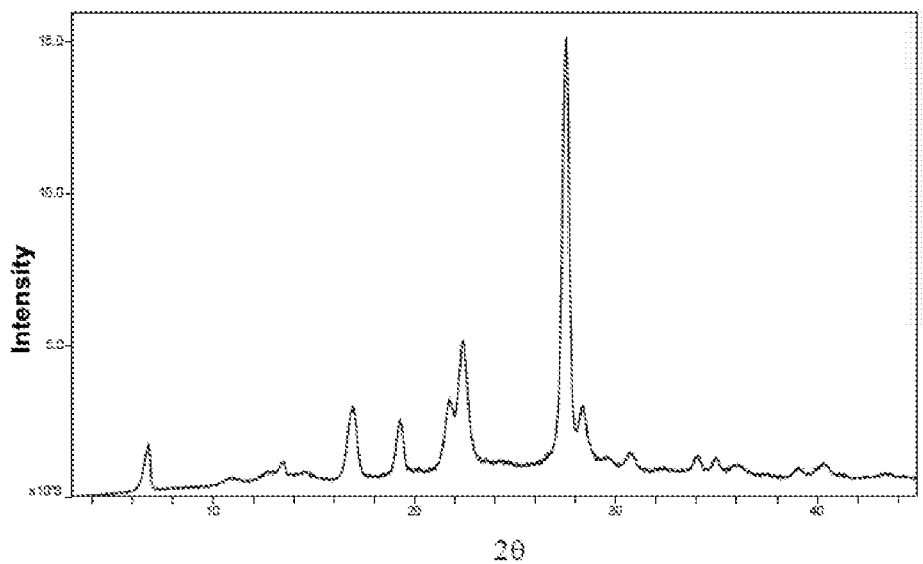
FIG. 7 shows an XRPD pattern of the illumination stability of 10 days for the crystalline Form A of pyrroloquinoline quinone betaine salt provided by the present invention.

Study on Illumination Stability of Crystalline Form A of Pyrroloquinoline Quinone Betaine Salt An appropriate amount of sample of the crystalline Form A of pyrroloquinoline quinone betaine salt was subjected to a light intensity of 4500 lux, and after 5 and 10 days the sample was removed for XPRD testing (as shown in FIGS. 6 and 7) to examine the crystalline stability of the sample under illumination. The results showed that the crystalline Form A of pyrroloquinoline quinone betaine salt was stable under illumination.

Comparative Example 1 Study on Stability of Pyrroloquinoline Quinone

The raw material PQQ obtained according to the Chinese invention patent CN 102596952 A was placed in an oven at 60° C. and 92.5% humidity and 4500 lux light intensity for stability testing in 5 and 10 days, respectively. The crystal transformation of the raw material PQQ was determined by XRPD.

Comparative Example 2 Study on Stability of Pyrroloquinoline Quinone Choline Salt According to the Chinese invention patent CN 103261197 A, 1.4 choline salt, 2 choline salt and 3 choline salt of PQQ were prepared. The dicholine salt of PQQ and the tricholine salt of PQQ were placed respectively in an oven at 60° C., under a humidity of 92.5% and a light intensity of 4500 lux, for stability testing for 5 days.

Figure 8:
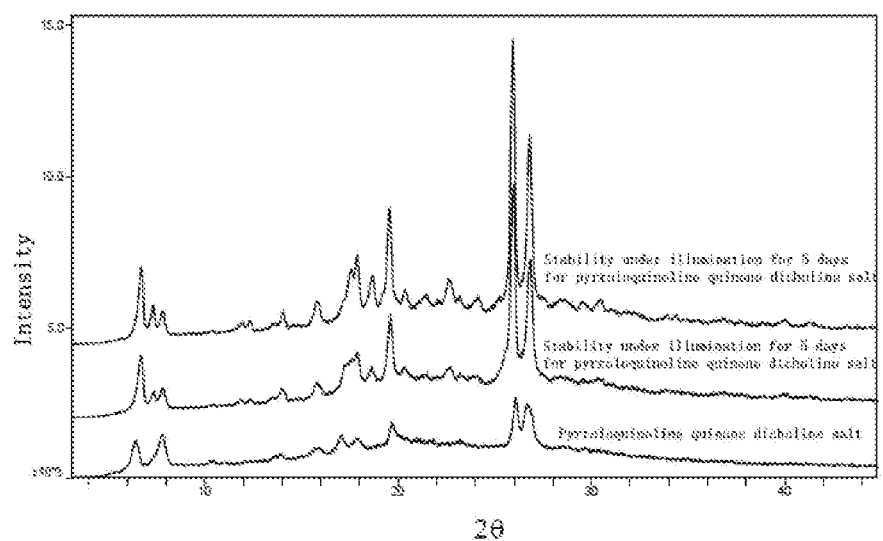
FIG. 8 shows an XRPD pattern of a prior dicholine salt of pyrroloquinoline quinone.

It was found that the dicholine salt of PQQ underwent a crystal transformation under high temperature and light conditions, and the dicholine salt of PQQ became water-soluble by absorbing water under high humidity conditions. The XRPD results are shown in FIG. 8.

However, the tricholine salt of PQQ became a sticky solid after standing for a period of time at room temperature (25°

C., about 50% humidity), proving that the tricholine salt of PQQ also had the problem of poor hygroscopicity.

Example 10

Figure 9:
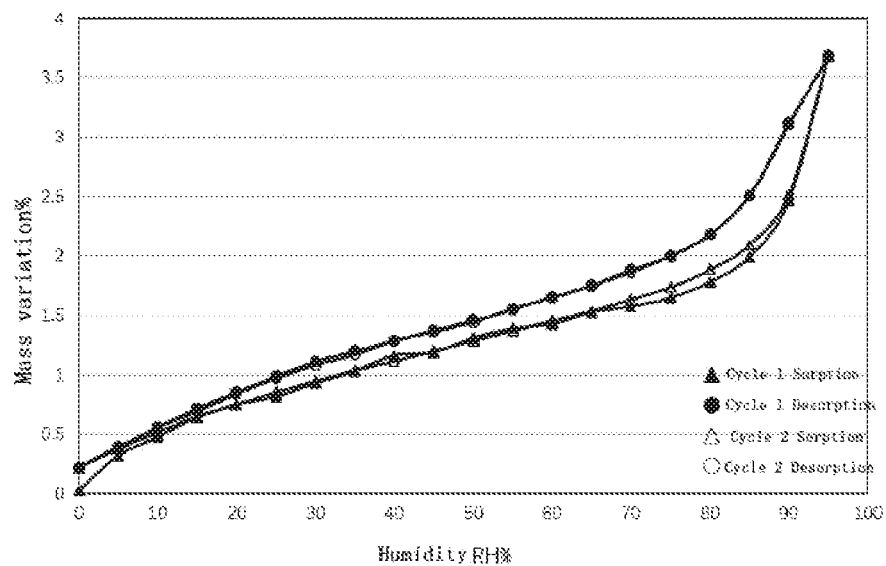
FIG. 9 shows a dynamic moisture sorption profile of the crystalline Form A of pyrroloquinoline quinone betaine salt provided by the present invention.
Figure 10:
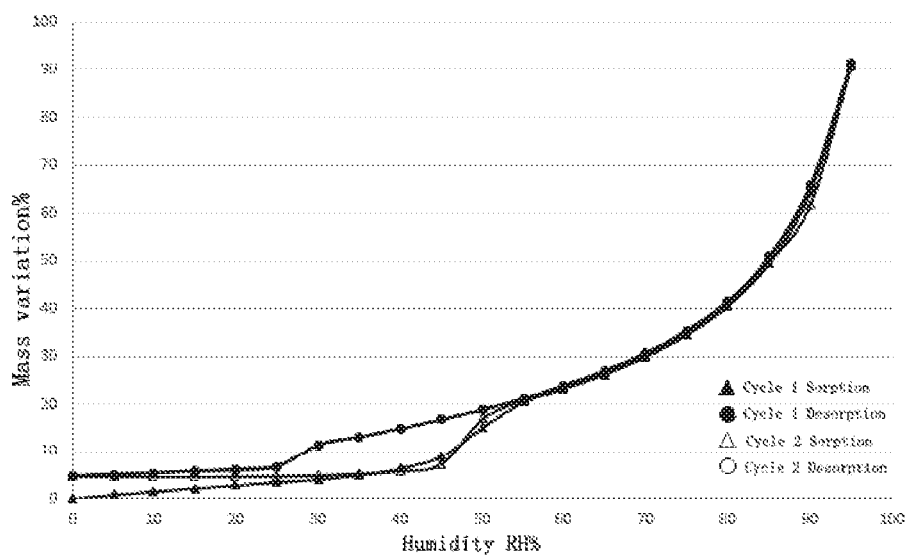
FIG. 10 shows a dynamic moisture sorption profile of a prior pyrroloquinoline quinone dicholine salt.

Comparison of Hygroscopicity of Pyrroloquinoline Quinone Betaine Salt and Dicholine Salt of PQQ The dynamic moisture sorption profiles of the crystalline Form A of pyrroloquinoline quinone betaine salt prepared in Example 1 and the dicholine salt of PQQ prepared in Comparative Example 2 were measured using an Intrinsic DVS from SMS, UK, respectively. The resulting dynamic moisture sorption profiles are shown in FIGS. 9 and 10, respectively.

The results showed that the dicholine salt of PQQ has a good hygroscopicity, which arriving at 7.4% in a warehouse environment (humidity of 45%); and the moisture sorption of betaine salt is only 1.1% under the same conditions. It is well known that samples with a good hygroscopicity can agglomerate during mixing of the samples, which has an effect on the uniformity of mixing.

Example 11

Solubility Evaluation of Crystalline Form A of Pyrroloquinoline Quinone Betaine Salt The crystalline Form A of pyrroloquinoline quinone betaine salt prepared in Example 1, the raw material PQQ of Comparative Example 1, 1.4 choline salt of PQQ prepared in Comparative Example 2, and disodium salt of PQQ prepared according to CN 102471336A were each formulated as a saturated aqueous solution at 30° C., for the saturated aqueous solution each, the absorbance at 450 nm was measured using an Agilent cary 60 ultraviolet spectrophotometer, and the solubility of pyrroloquinoline quinone was determined by the ultraviolet-visible absorption spectroscopy. The results are shown in Table 2.

TABLE 2

| Comparison of Solubility of Different Pyrroloquinoline Quinone Salts | | |
|---|---|---|
| PQQ salt | Solubility (mmol/L) | Relative ratio |
| Crystalline Form A of PQQ betaine salt | 14.50 | 1.50 |
| PQQ in the free form | 1.41 | 0.15 |
| 1.4 Choline salt of PQQ | 9.68 | 1.00 |
| Disodium salt of PQQ | 10.00 | 1.03 |

The results showed that the crystalline Form A of pyrroloquinoline quinone betaine salt provided by the invention has a good solubility and is superior to the existing PQQ in solid form.

Example 12

TGA Detection of Crystalline Form A of Pyrroloquinoline Quinone Betaine Salt

Figure 11:
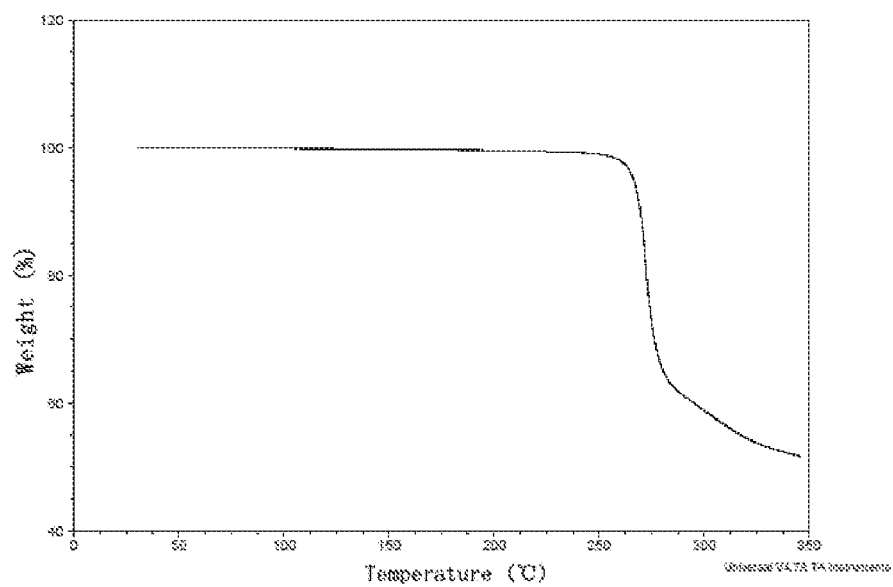
FIG. 11 shows a TGA profile of the crystalline Form A of pyrroloquinoline quinone betaine salt provided by the present invention.

The crystalline Form A of pyrroloquinoline quinone betaine salt of Example 1 was tested for the TGA profile under standard conditions using a Q500 thermal analyzer from TA Corporation, USA. The test was carried out under the conditions as follows: rate of temperature increasing: 10° C./min; temperature range: 30° C. to 350° C. The resulting TGA profile is shown in FIG. 11.

The results showed that the residual amount of solvent ethanol in the crystalline Form A of pyrroloquinoline quinone betaine salt provided by the present invention is 0.09%.

In summary, the crystalline Form A of pyrroloquinoline quinone betaine salt can maintain stable under the conditions of high temperature, high humidity and illumination, and is superior to the existing PQQ in the free form and other PQQ salts. Stable crystalline forms have advantages in the manufacture of pharmaceutical formulations. Due to the stability of the crystalline Form A of pyrroloquinoline quinone betaine salt, it can maintain stable in the process of producing drugs in various solid dosage forms, the crystalline form of the drug active ingredient in the finally obtained drug can be determined, the known bioavailability can be ensured, and the pharmacodynamical difference caused by the crystalline transformation will not occur.

Example 13

Effect of Pyrroloquinoline Quinone Betaine Salt on ALT and AST in Serum and SOD, GSH-Px and MDA in Liver Homogenate for CC14-Induced Acute Liver Injury Model Mice Forty-eight male Kunming mice weighing 18-22 g were randomly divided into 4 groups: blank control group, CC14 model group, PQQ disodium salt group and PQQ betaine salt group, respectively, with 12 mice in each group. The blank control group and the model group were administered with distilled water by gavage, the PQQ disodium salt group (3 mg/kg, by weight of PQQ) and the PQQ betaine salt group (3 mg/kg, by weight of PQQ, the PQQ betaine salt used was the crystalline Form A of pyrroloquinoline quinone betaine salt prepared according to the method described in Example 1) were administered with drugs respectively by gavage once a day and for 7 days continuously.

On the 7th day after gavage for 1 h, the mice in CC14 model group, PQQ disodium salt group and PQQ betaine salt group were injected intraperitoneally with 0.25% CC14 peanut oil (10 mL/kg) once, resulting in acute liver injury models; while mice in the blank control group were injected intraperitoneally with peanut oil (10 mL/kg) once. Animals were sacrificed after orbital blood collection for 24 h. 0.5-1 mL blood was collected from the mouse orbit, serum was separated by static centrifugation, and ALT and AST levels in serum were measured by biochemical kits. Animals were sacrificed and livers were removed for preparing liver homogenate. Superoxide dismutase (SOD), glutathione peroxidase (GSH-Px) activity and malondialdehyde (MDA) content in liver homogenates were determined by biochemical kits. The results are shown in Table 3.

TABLE 3

ALT and AST in Serum and SOD, GSH-Px and MDA (Mean ± SD)
in Liver Homogenate for CC14-induced Acute Liver Injury Model Mice

| Group | ALT(IU/L) | AST(IU/L) | SOD (kU/g pro) | GSH-Px(kU/g pro) | MDA (nmol/L) |
|---|---|---|---|---|---|
| Blank control group | 39.2 ± 6.5 | 41.5 ± 8.2 | 43.7 ± 5.9 | 104.9 ± 9.1 | 2.15 ± 0.33 |
| Model group | 160.3 ± 36.5** | 140.4 ± 33.9** | 25.0 ± 4.4** | 76.1 ± 6.2** | 3.04 ± 0.43** |
| PQQ disodium salt group (3 mg/kg) | 126.5 ± 27.0$^{\Delta\Delta}$ | 115.4 ± 22.7$^{\Delta}$ | 29.5 ± 4.9$^{\Delta}$ | 93.4 ± 10.1$^{\Delta\Delta}$ | 2.71 ± 0.37$^{\Delta}$ |
| PQQ betaine salt group (3 mg/kg) | 110.1 ± 26.0$^{\Delta\Delta}$ | 110.0 ± 20.4$^{\Delta\Delta}$ | 31.1 ± 4.5$^{\Delta\Delta}$ | 93.5 ± 9.0$^{\Delta\Delta}$ | 2.61 ± 0.37$^{\Delta\Delta}$ |

* $P < 0.05$,
**$P < 0.01$, compared with blank control group;
$^{\Delta}P < 0.05$,
$^{\Delta\Delta}P < 0.01$ compared with model group.

As seen from Table 3, after mice were injected intraperitoneally with CC14 peanut oil solution for 24 hours, the levels of ALT and AST in serum increased, the activities of SOD and GSH-Px in liver homogenate decreased, and the content of MDA increased (each P<0.01). Compared with mice in the model group, ALT and AST levels in mice serum in PQQ betaine salt group decreased, SOD and GSH-Px activities in liver homogenate increased, and MDA content decreased (each of P<0.01); furthermore, the improvement effect of PQQ betaine salt on ALT, GSH-Px and MDA was better than that of PQQ disodium salt. The results showed that PQQ betaine salt significantly improved CC14-induced acute liver injury in mice.

Example 14 Effect of Pyrroloquinoline Quinone Betaine Salt on Learning and Memory of Scopolamine-Induced Memory Disordered Model Mice Fifty Kunming mice, weighing 18-22 g, were randomly divided into five groups: blank control group, model group, low-dose PQQ betaine salt group (1.5 mg/kg), high-dose PQQ betaine salt group (3 mg/kg) and positive control group (donepezil, 3 mg/kg), respectively, 10 mice in each group. Wherein the PQQ betaine salt used is a crystalline Form A of pyrroloquinoline quinone betaine salt prepared according to the method of example 1.

The blank control group and the model group were administered with distilled water by gavage, the low-dose PQQ betaine salt group, the high-dose group and positive control group were administered with drugs by gavage respectively, once a day. Learning and memory training was carried out on the fifth day of administration and for 5 days in total; the model group, the low-dose PQQ betaine salt group, the high-dose group and the positive control group were intraperitoneally injected with 2 mg/kg of scopolamine 20 minutes earlier before training to obtain memory disordered models, while the blank control group was injected with a corresponding volume of saline. Morris water maze experiment were carried out for 5 days in total, wherein, a place navigation test was carried out in the first 4 days in order to observe and record the time required for the experimental animals to seek and climb onto the platform, in order to test the learning ability of mice. On the fifth day, a spatial probe test was carried out, during the test, the platform was removed, the time (the latent period) when crossing the original platform position for the first time was recorded as well as the number of time of traversing the original platform position for the animal, in order to test the spatial memory capacity of the animal. The latent period and the number of time of traversing platforms were used as evaluation indexes to detect the improvement of learning and memory in dementia model mice.

The results of the place navigation experiments are shown in Table 4. The platform-finding time (latent period) of experimental animals in each group was gradually shortened with the training. Compared with the blank control group, the latent period of the model group became significantly longer from the beginning of the third day (P<0.01). After the mice were administered with PQQ betaine, the spatial learning and memory disorders caused by scopolamine were improved, the latent period was significantly shortened, and the difference was statistically significant compared with the model group (P<0.05 or P<0.01).

TABLE 4

Effect of Pyrroloquinoline Quinone Betaine Salt on Time (latent period) Required to Climb onto thePlatform During Memory Training (Mean ± SD) for Scopolamine-induced Memory Disordered Mice

| | Latent period(s) | | | |
|---|---|---|---|---|
| Group | The first day | The second day | The third day | The fourth day |
| Blank control | 72.10 ± 16.16 | 60.60 ± 12.61 | 31.80 ± 12.73 | 26.40 ± 8.91 |
| Model | | | | |
| PQQ betaine salt(1.5 mg/kg) | 74.30 ± 17.80 | 62.90 ± 14.07 | 51.90 ± 16.43** | 50.80 ± 15.95** |

TABLE 4-continued

Effect of Pyrroloquinoline Quinone Betaine Salt on Time (latent period) Required to Climb onto thePlatform During Memory Training (Mean ± SD) for Scopolamine-induced Memory Disordered Mice

| Group | Latent period(s) | | | |
|---|---|---|---|---|
| | The first day | The second day | The third day | The fourth day |
| PQQ betaine salt(3 mg/kg) | 74.70 ± 16.94 | 62.30 ± 13.84 | 38.20 ± 14.01$^\Delta$ | 29.50 ± 12.29$^{\Delta\Delta}$ |
| Donepezil(3 mg/kg) | 76.60 ± 18.35 | 68.70 ± 13.98 | 37.10 ± 13.08$^\Delta$ | 29.30 ± 10.12$^{\Delta\Delta}$ |
| | 69.50 ± 17.23 | 53.00 ± 13.06 | 37.10 ± 12.22$^\Delta$ | 27.20 ± 11.01$^{\Delta\Delta}$ |

\* $P < 0.05$,
\*\*$P < 0.01$, compared with the blank control group;
$^\Delta p < 0.05$,
$^{\Delta\Delta}p < 0.01$ compared with the model group.

The results of the spatial search experiments are shown in Table 5. Compared with the blank control group, the latent period of the model group was significantly longer than that of the control group, and the number of time of crossing platform was significantly reduced, the difference was statistically significant ($P<0.01$). The latent period of animals in the group administered with PQQ betaine salt was reduced and the number of time of crossing platform was increased, the difference was statistically significant compared to the model group ($P<0.05$).

TABLE 5

Effect of Pyrroloquinoline Quinone Betaine Salt on Time (Latent Period) of Crossing the Original Platform and Number of Time of Crossing the Original Platform (Mean ± SD) for Scopolamine-Induced Memory Disordered Mice

| Group | Latent period(s) | Number of time of crossing platform |
|---|---|---|
| Blank control group | 8.21 ± 4.44 | 5.20 ± 1.62 |
| Model group | 59.63 ± 20.06\*\* | 0.70 ± 0.87\*\* |
| PQQ betaine salt group(1.5 mg/kg) | 25.48 ± 12.19$^{\Delta\Delta}$ | 2.20 ± 0.42$^\Delta$ |
| PQQ betaine salt group(3 mg/kg) | 20.98 ± 9.44$^{\Delta\Delta}$ | 2.10 ± 0.57$^\Delta$ |
| Donepezil(3 mg/kg) | 16.41 ± 7.60$^{\Delta\Delta}$ | 2.90 ± 0.57$^{\Delta\Delta}$ |

\* $P < 0.05$,
\*\*$P < 0.01$, compared with the blank control group;
$^\Delta p < 0.05$,
$^{\Delta\Delta}p < 0.01$ compared with the model group.

Taken the results of above animal experiments together, it showed that the pyrroloquinoline quinone betaine salt of the present invention could simultaneously provide two beneficial substances: PQQ and betaine; and betaine could have a synergistic effect on the function of PQQ after being salified with PQQ.

Example 15

Preparation of Pyrroloquinoline Quinone Betaine Salt Composition Capsules

Formulation: PQQ Betaine salt 20 mg.
Cellulose powder 100 mg.
Micropowder silica gel 2 mg.
The process comprises the following steps to obtain the capsule: taking the PQQ salt for crushing to sift through a 100 mesh sieve; adding silica gel micropowder thereto and mixing uniformly, followed by adding cellulose powder thereto and mixing uniformly, and filling the mixture into No. 4 of capsule.

Example 16

Preparation of Pyrroloquinoline Quinone Betaine Salt Composition Capsules

Formulation: PQQ Betaine salt 20 mg.
Coenzyme Q10 100 mg.
Microcrystalline cellulose 50 mg.
Betacyclodextrin 100 mg.
Silica gel micropowder 2 mg.
The process comprises the following steps: putting PQQ salt, coenzyme Q10, betacyclodextrin and microcrystalline cellulose together into a ball mill for grinding and crushing. The ground powder was removed and added silica gel micropowder thereto and mixed uniformly, and then the mixture was filled into No. 2 of capsule to obtain the composition capsule.

Example 17

Preparation of Pyrroloquinoline Quinone Betaine Salt Composition Tablets

Formulation: PQQ Betaine salt 20 mg.
Microcrystalline cellulose 60 mg.
Compressible starch 60 mg.
Calcium hydrogen phosphate 50 mg.
Sodium carboxymethyl starch 10 mg.
2% hydroxypropylmethyl cellulose q.s.
Silica gel micropowder 2 mg.
Magnesium stearate 1 mg.
The process comprises the following steps: crushing and sieving PQQ salt, microcrystalline cellulose, compressible starch, dibasic calcium phosphate and sodium carboxymethyl starch, respectively; mixing the above powder and adding a proper amount of 2% hydroxypropyl methyl cellulose to prepare a soft material; sifting through a 20 mesh sieve to obtain wet particles and drying at 50° C.; after granulation, adding silica gel micropowder and magnesium stearate for mixing in total, and applying a stamping sheet with the diameter of 8 mm.

Example 18

Preparation of Pyrroloquinoline Quinone Betaine Salt Composition Soft Capsules

Formulation: PQQ Betaine salt 20 mg.

Corn oil 200 mg.

Vitamin E 10 mg.

Vitamin C Palmitate 0.1 mg.

Formulation of Skin of Capsule: Gelatin 2 parts.

Glycerol 1 part.

Sorbitol 0.5 part.

Pure water 1.5 parts.

Titanium dioxide 0.04 part.

The process comprises the following steps: (1) injecting glycerol, sorbitol and pure water into a sol tank, heating to 70° C. and stirring at the temperature, then adding gelatinized glue; dispersing titanium dioxide in a colloid mill, adding pigment if necessary, and then adding glue solution; after stirring uniformly, defoaming under vacuum. (2) weighing the various contents respectively and co-grounding in a ball mill. (3) pressing and shaping the obtained above into capsules by a capsule machine to prepare soft capsules.

In Examples 15-18, the PQQ betaine salt used includes, but is not limited to, the Form A of pyrroloquinoline quinone betaine salt prepared according to the method described in Example 1.

It will be appreciated by those skilled in the art that, although specific embodiments of the invention have been described herein for purposes of illustration, various modifications may be made without departing from the spirit and scope of the invention. Therefore, specific embodiments and examples of the invention should not be construed as limiting the scope of the invention. The invention is limited only by the following claims. All documents cited in this application are incorporated herein by reference in their entirety.

The invention claimed is:

1. A pyrroloquinoline quinone betaine salt of formula (I), wherein n is 0.5 to 3.

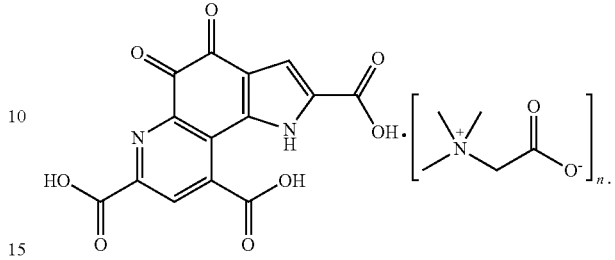

(I)

2. The pyrroloquinoline quinone betaine salt of claim 1, wherein n is 1.

3. A crystalline Form A of the pyrroloquinoline quinone betaine salt of formula (II), characterized by an XRPD pattern having diffraction peaks at 2θ of 6.721, 13.424, 16.941, 19.28, 21.7, 22.42, 27.5, 28.36, wherein the error range of the 2θ values is ±0.2.

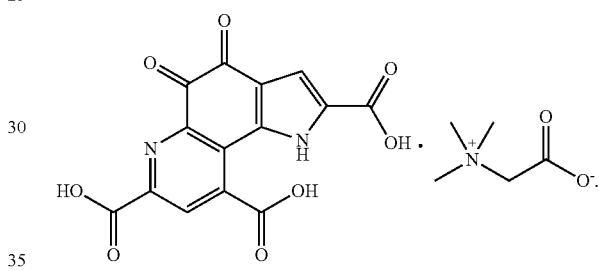

(II)

4. The crystalline Form A of pyrroloquinoline quinone betaine salt of claim 3, having an XRPD pattern substantially the same as FIG. 1 of the accompanying drawings.

5. A method for preparing the pyrroloquinoline quinone betaine salt according to claim 1, comprising the steps of: (1) dissolving pyrroloquinoline quinone in an organic solvent, and adding betaine thereto to obtain a suspension liquid; (2) stirring the suspension liquid at 25-35° C., followed by filtering and drying to obtain a solid.

6. The preparation method according to claim 5, wherein the organic solvent is ethanol.

7. A composition comprising the pyrroloquinoline quinone betaine salt of claim 1 and one or more pharmaceutically acceptable carriers, excipients or diluents.

* * * * *